United States Patent
Dow et al.

(10) Patent No.: US 6,723,050 B2
(45) Date of Patent: Apr. 20, 2004

(54) VOLUME RENDERED THREE DIMENSIONAL ULTRASONIC IMAGES WITH POLAR COORDINATES

(75) Inventors: Alasdair Dow, Snohomish, WA (US); Paul R. Detmer, Seattle, WA (US); Jing-Ming Jong, Seattle, WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/026,996

(22) Filed: Dec. 19, 2001

(65) Prior Publication Data

US 2003/0114757 A1 Jun. 19, 2003

(51) Int. Cl.[7] ................................................. A61B 8/00
(52) U.S. Cl. ..................................................... 600/443
(58) Field of Search ................................ 600/407–471; 128/916; 367/7, 11, 130, 138; 73/625, 626; 382/128–133

(56) References Cited

U.S. PATENT DOCUMENTS

| | | |
|---|---|---|
| 4,582,065 A | 4/1986 | Adams |
| 5,159,931 A | 11/1992 | Pini |
| 5,181,514 A | 1/1993 | Solomon et al. |
| 5,329,929 A | 7/1994 | Sato |
| 5,462,057 A * | 10/1995 | Hunt et al. .................. 600/447 |
| 5,474,073 A | 12/1995 | Schwartz et al. |
| 5,647,360 A * | 7/1997 | Bani-Hashemi et al. ..... 600/425 |
| 5,787,889 A * | 8/1998 | Edwards et al. ............ 600/443 |
| 5,797,846 A | 8/1998 | Seyed-Bolorforosh et al. |
| 5,846,200 A | 12/1998 | Schwartz |
| 5,865,750 A | 2/1999 | Hatfield et al. |
| 5,967,985 A | 10/1999 | Hayakawa |
| 6,139,498 A * | 10/2000 | Katsman et al. ............ 600/443 |
| 6,500,123 B1 * | 12/2002 | Holloway et al. .......... 600/443 |

OTHER PUBLICATIONS

Lee et al., "Analysis of a Scan Conversion Algorithm for a Real-Time Sectpr Scanner," IEEE Trans. on Med. Imag., Vol MI-5, No. 2, Jun. 1986, pp. 96–105.

* cited by examiner

*Primary Examiner*—Ali M. Imam
(74) *Attorney, Agent, or Firm*—W. Brinton Yorks, Jr.

(57) ABSTRACT

Three dimensional ultrasonic images are formed by volume rendering using a 3D ultrasonic image data set. The data set may be acquired by rocking, sweeping, fanning or rotating a 2D image plane through the volume being scanned, or by steering beams in different angular directions from a two dimensional array of transducer elements. The polar data is volume rendered to form a 3D image by means of projected raylines which are warped to account for the angular geometry of the acquisition.

19 Claims, 4 Drawing Sheets

VOLUME RENDERED THREE DIMENSIONAL ULTRASONIC IMAGES WITH POLAR COORDINATES

This invention relates to ultrasonic diagnostic imaging systems and, in particular, to ultrasonic diagnostic imaging systems which produce volume rendered three dimensional images from polar coordinate image data.

Ultrasonic diagnostic imaging has reached a stage of evolution where real time three dimensional (3D) imaging is approaching practical reality. In 3D imaging the ultrasonic transducer scans a volumetric region to acquire a 3D set of ultrasonic echo data which adequately samples the volume. The 3D data set may be acquired by means of a one dimensional array which scans an image plane while the array is moved to sweep the image plane through the volumetric region. The 3D data set may also be acquired by means of a two dimensional array which electronically steers beams in three dimensions through the volumetric region. The 3D echo data set is then processed to form an image of the three dimensional region which can be displayed on a display device.

Since the display devices currently in use in ultrasound are monitors and flat panel displays, consideration must be given to the method for presenting a display of 3D information on a two dimensional display medium. Several types of 3D images may be formed from a data set. One is a projection, orthographic, or perspective view formed by the process known as volume rendering. Volume rendering is a technique for composing a set of samples in 3D space into a single 2D image for visualization. This is done by projecting a series of parallel raylines through the 3D data set from the perspective of a viewer who is viewing the volumetric region in the direction of the raylines, and accumulating some function of the voxels along each rayline. Each time a partial or complete new 3D data set is acquired the data must be rendered to create the next real time image in the sequence. Volume rendering is described in U.S. Pat. Nos. 5,474,073 and 5,329,929, for instance. Another 3D display technique is called multi-planar reformatting (MPR), by which one or more 2D image planes through the volumetric region are displayed.

Traditionally volume rendering or multi-planar reformatting is performed on 3D data samples or "voxels" which are arranged in a rectilinear grid in the spatial domain. There are a number of 3D acquisition methodologies, such as apparatus which acquires a sequence of parallel planes of parallel (linear) scanlines, which will directly produce 3D echo data in a rectilinear format. However, there are other acquisition methodologies that rotate or angularly fan a transducer array to scan a 3D volume which do not produce rectilinearly distributed echo data. Such data generally has polar or spherical coordinates in which individual scanlines or planes have an angular relation to a reference axis. Electronically scanned 2D arrays which scan a conical or pyramidal volume will produce 3D data with the same polar characteristic. In order to apply a conventional volume rendering algorithm to the data, it must first be converted to rectilinear or Cartesian coordinates. This process, which may be described as 3D scan conversion, is very computation intensive. Furthermore, the volume rendering algorithm may only need to operate on a portion of the 3D data set, meaning that much of the 3D scan conversion was unnecessary. Accordingly it is desirable to be able to do volume rendering of a 3D data set without performing needless, time-consuming scan conversion, and preferably without doing scan conversion at all.

In accordance with the principles of the present invention, volume rendering is performed directly on polar 3D ultrasound image data without the need for prior conversion to Cartesian coordinates. This is accomplished by warping the projected raylines of the rendering process to account for the physical relationship of the data. For example, instead of using parallel linear raylines, curved raylines are employed with a curvature which is a function of the scan acquisition geometry. The invention lends itself well to 3D ultrasonic imaging systems where high speed or low cost are desired.

In the drawings:

FIG. 8 is a spatial representation of image data planes a,b,c, . . . n seen edge-on.

Figure 1:
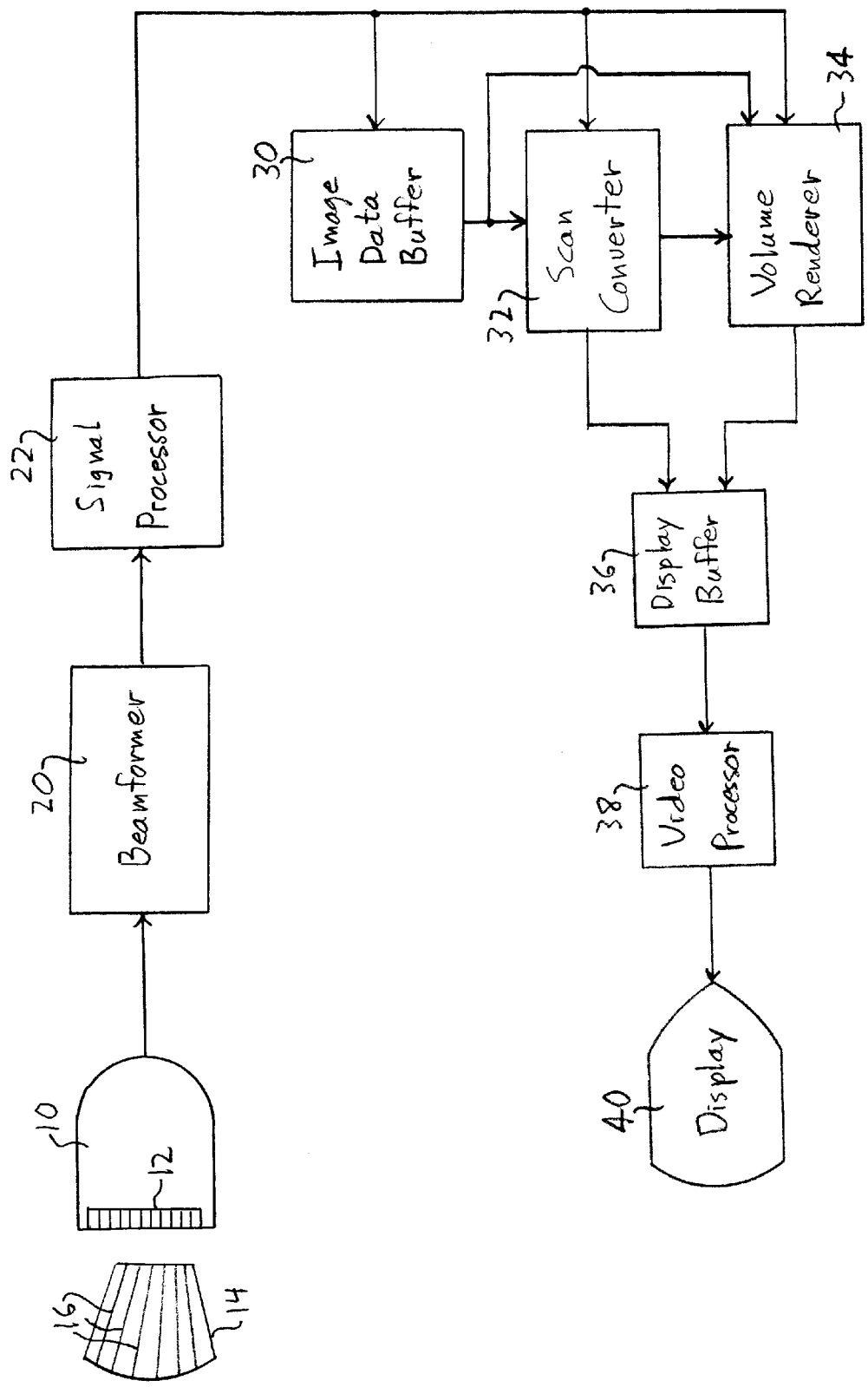
FIG. 1 illustrates in block diagram form a diagnostic ultrasound system constructed in accordance with the principles of the present invention.

Referring first to FIG. 1, an ultrasound system constructed in accordance with the principles of the present invention is shown. A probe 10 contains a transducer array 12 which transmits and receives ultrasonic scanlines 16 over an image field. The array 12 can extend in one row or dimension and thus be capable of scanning over a single plane in front of the probe. The shape of the plane 14 can be rectangular or sector-shaped or trapezoidal as shown in the drawing, depending upon the steering of the scanlines. If only a plane is scanned, the probe must be moved by rocking or rotating or translation to sweep the plane through a volumetric region for 3D scanning. When a two-dimensional array is used, scanlines can be steered electronically in a 3D volume in front of the probe. Received scanlines are coupled to a beamformer 20 which combines echo signals from individual transducer elements into coherent echo signals along one or several scanline directions. The beamformer 20 also controls the transmission of beams by the probe. The received echo signals are processed by a signal processor which may produce signals of a particular mode of operation such as fundamental, harmonic, or Doppler mode. The processed signals are then stored in an image data buffer 30. Data elements of a 3D data set would generally be stored in the image data buffer with addresses of the form r,φ,θ or r,θ,z, for example.

When two dimensional imaging is being performed the image data acquired from a particular plane is scan converted by a scan converter 32. The scan converter will take polar (r,θ) data and map it to Cartesian coordinates, usually by four-point (or eight-point) interpolation as described in U.S. Pat. No. 4,581,636. The interpolation not only results in a data set mapped to Cartesian (x,y) coordinates, but also maps a data set which is scaled in all dimensions of the image for the desired display format. That is, the data points are appropriately spaced in both x and y dimensions, thus providing a uniform pixel distribution for an image. The scan converted image data is stored in a display buffer 36 from which it is processed for display on a display 40 by a video processor 38.

Figure 3:
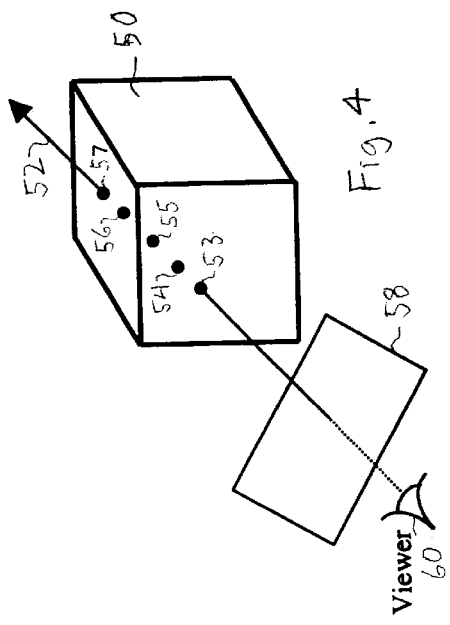
FIG. 3 illustrates a 3D data set of ultrasonic image planes.
Figure 2:
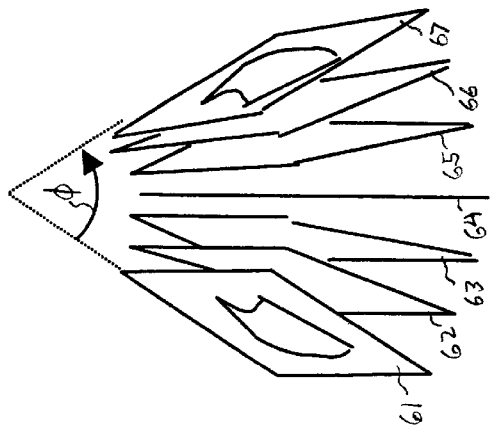
FIG. 2 illustrates the acquisition of parallel image planes for a 3D data set.

For three dimensional imaging the probe 10 can be linearly translated to sweep the image plane 14 through a series of parallel plane positions in the volume being imaged. The image planes are then acquired in a sequence of parallel planes 1, 2, ... N as shown in FIG. 2. If the scanlines of a given plane have an angular variation such as a sector image, scan conversion is performed by the scan converter 32 to convert the polar scanline data into a Cartesian coordinate image. The resulting 3D data set of the parallel planes would appear as illustrated by the rectilinear grid "cube" of data 50 shown in FIG. 3. The image 14 of the first plane of the data set is shown on the front surface of the cube. Since the planes were acquired in parallel the data is conveniently arranged in a Cartesian coordinate system in the elevation (z) dimension, with the x,y,z coordinates shown in the drawing. The 3D data set is now operated on by a volume renderer 34 to produce an image of the information for display on a display screen 40.

Figure 4:
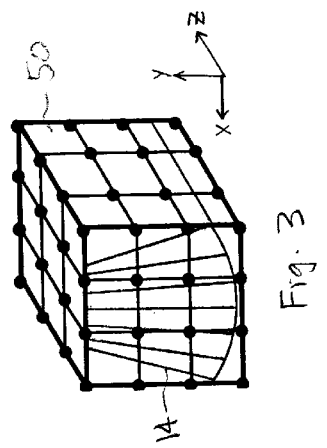
FIG. 4 illustrates the principle of volume rendering.

The volume rendering process is depicted by FIG. 4. In volume rendering a series of raylines are projected through the data set 50 from the perspective of a viewer 60. The 3D image will appear differently as a function of the perspective from which the 3D object is viewed. One of the raylines 52 is shown in FIG. 4. As the raylines pass through the data set they encounter a series of data points or voxels along the path of the rayline. Five such voxels 53–57 are shown being intersected by the rayline 52 as it passes through the data set. The rendering algorithm accumulates the values of the voxels along the rayline, then projects the accumulated value as an image point on a plane 58 where the viewer 60 is located. The 3D image thus assembled on the plane 58 is displayed on the display 40.

The rendering algorithm may accumulate the values of the data points in any of a number of functional operations such as compositing, integration, averaging, peak detection, or others. The values may be weighted as a function of their distance from the viewer and/or the spacing between the data points along the rayline.

Figure 5:
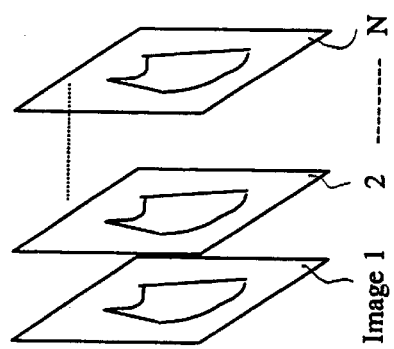
FIG. 5 illustrates a fanned acquisition of 3D ultrasonic image data.
Figure 6:
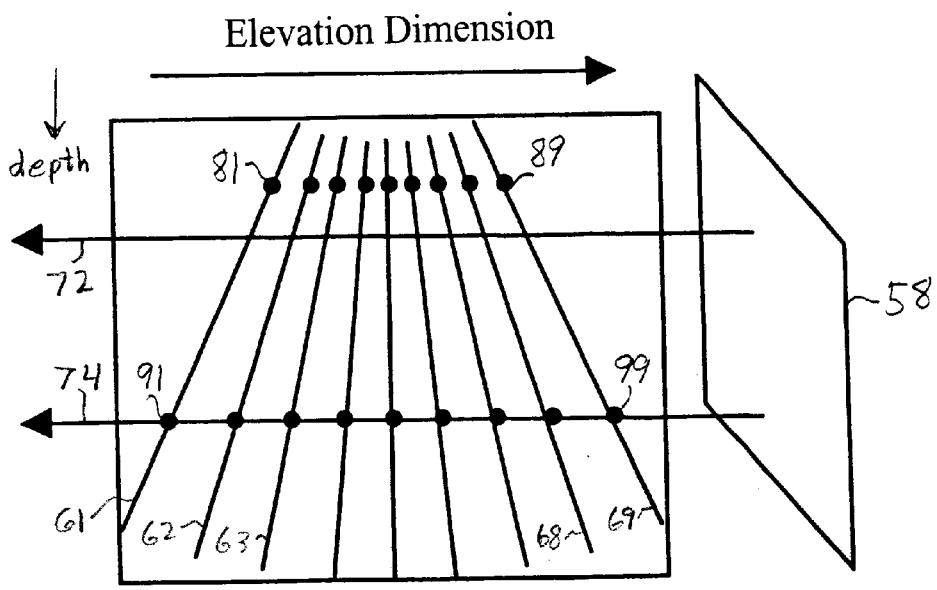
FIG. 6 illustrates the volume rendering of partially scan converted image planes.

However, 3D data acquisition is not always performed by parallel plane acquisition. The probe may be rocked or rotated to sweep a two dimensional plane through the volume to be viewed. In that case a series of angularly disposed planes 61–67 may be acquired as shown in FIG. 5, in which a probe is rocked or rotated to sweep the image plane through an angle $\phi$. Alternatively a series of angularly disposed scanlines may be acquired from a volume by use of a two dimensional phased array. In either case the scanlines are related by polar coordinates indicating their angle of inclination relative to a reference axis. In order to view such polar data in a three dimensional display two processing steps are necessary: first, the data must be scan converted to a rectilinear grid such as that of FIG. 3, then must be rendered as shown in FIG. 4. The computational requirements of three dimensional scan conversion are substantial, particularly when considering that the rendering algorithm may operate on only a subset of the scan converted data for 3D image formation. For real time three dimensional imaging this may necessitate the use of dedicated scan conversion hardware which is expensive as compared with software implementations to scan conversion. After the scan conversion process volume rendering may be performed by projecting raylines 72, 74, etc. through the scan converted 3D data set as shown in FIG. 6, and accumulating 3D display values along the raylines for a display plane 58. In this drawing the elevation dimension is the plane-to-plane dimension and the image planes 61–69 are viewed edge-on in the drawing.

Figure 7:
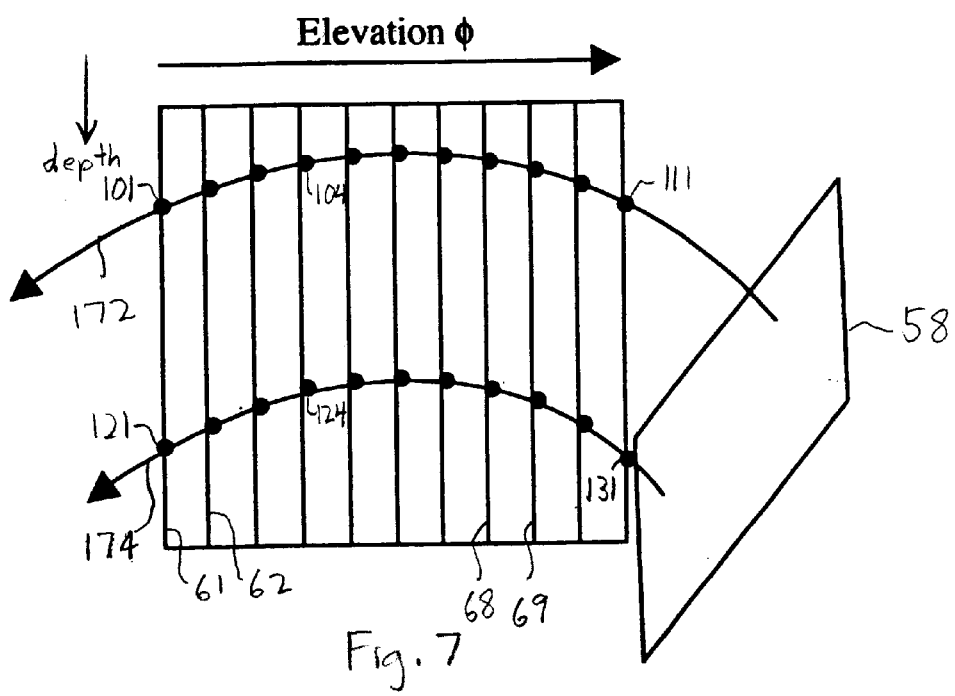
FIG. 7 illustrates the volume rendering of 3D polar data in accordance with the principles of the present invention.

In accordance with the principles of the present invention, the computationally intensive scan conversion process is obviated by performing volume rendering directly on the 3D polar data without scan conversion. As FIG. 6 shows, the projection raylines 72,74 of the volume rendering operation are straight when the 3D data set has been scan converted into spatially related Cartesian coordinates. The raylines are just illustrative, of course: in an actual embodiment the data points along a "rayline" are chosen by selectively addressing points which, in the physical space of the object, would be located in a straight line. In accordance with the principles of the present invention, scan conversion is obviated by incorporating the geometry of the acquired data into the volume rendering function. This is represented graphically in FIG. 7, in which the raylines 172,174 for volume rendering are curved as a function of the acquisition geometry. The planes 61, 62, 68, 69, ... in FIG. 7 are shown edge-on in parallel, representing that no scan conversion was performed to account for the angle $\phi$ through which the probe was swept to acquire them. The raylines 172,174 are now curved as shown in the drawing as a function of the data acquisition angle $\phi$. In a constructed embodiment, since there are no physical "raylines" as such, the curved sequence of the data points or voxels along the "raylines" is produced by taking the acquisition angle $\phi$ into consideration in addressing the voxels to be accumulated for a rendered display data point. The voxels along each curved rayline are accumulated by the rendering function (averaging, integrating, etc.) to produce 3D image display pixels on the display 40. The voxels 101–111 encountered along curved rayline 172 are accumulated to produce one pixel of the image in the projection plane 58, and the voxels 121–131 encountered along curved rayline 174 are accumulated to produce another pixel on the projection plane 58, for example. Thus, the rendering process accounts for the geometry of the acquired data and there is no need to scan convert the 3D data prior to volume rendering.

The type of ultrasound image data which can be processed by the technique of the present invention can be tissue image data, flow image data, or image data containing both tissue and flow information. When tissue information is processed for 3D display, an opacity control variable is generally employed to enable the viewer to see into the volume of tissue; otherwise, the interior of the volume is obscured beyond the outer surface of the volume. When opacity-based rendering is performed, the viewer may only be able to see a small distance into the volume, as the rendering process causes deeper depths to be obscured. This is an effect provided by the chosen accumulation function. A result of this is that only a relatively small number of the data points along a rayline need to be used in the rendering process, as points deeper within the volume are obscured from view. The technique of the present invention is especially efficient in such opacity-based renderings, where only a portion of all data points are used in the rendering operation. This is because much of the effort of 3D scan conversion, which scan converts all of the data in the volume, is wasted because only a portion of the converted data is used. Use of the present invention avoids this wasted effort.

When a pyramidal or trapezoidal acquisition is used as illustrated in FIGS. 5 and 6, the data points at the top of the pyramid or trapezoid are closer together in the horizontal (plane-to-plane) dimension than data points at greater depths. Compare the spacing of shallow data points 81–89 with the spacing of deeper data points 61–69 in FIG. 6. This nonuniform spacing is generally eliminated by the scan conversion process, which usually produces a grid of data points which are uniformly spaced in all dimensions. This results in uniform step sizes from data point to data point along a rayline during rendering, producing a uniformly rendered 3D image. In FIG. 7 the acquired planes are shown in parallel, giving the appearance that the data points 101–111 along shallow rayline 172 traverse the same spatial distance in the same step size as do data points 121–131 along the deeper rayline 121. This is not the case, of course, as the data is polar and hence the step size along rayline 172 is actually less than the step size along rayline 174. This difference in step size can be taken into consideration in the rendering operation by, for example, weighting of the data that is accumulated. Thus, to render a given distance into the volume, fewer data points along rayline 174 would be used than data points along rayline 172. Alternatively, the step size could be kept constant in physical space and the sampling done at variable intervals in polar space.

Figure 8:
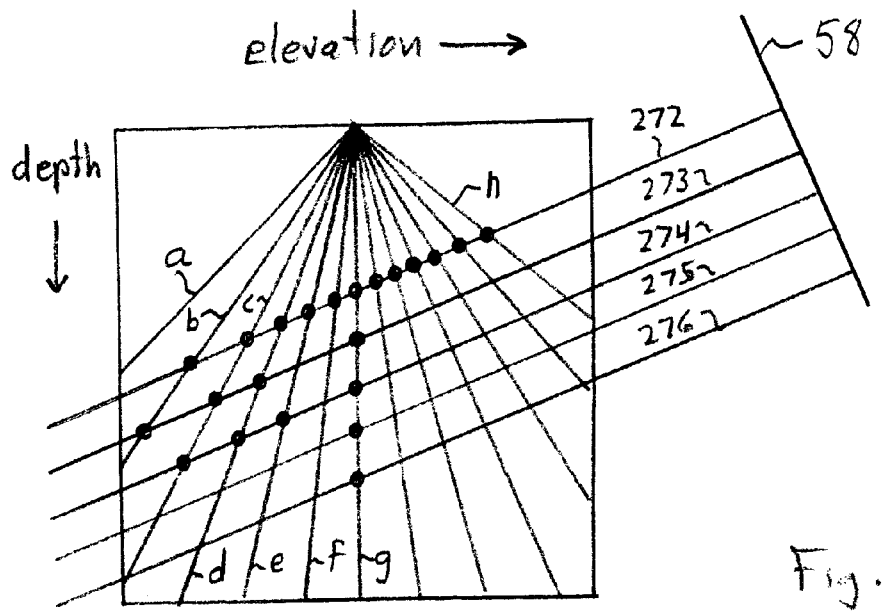

Changing the sampling clock timing along the raylines to align it with respect to the viewpoint will also render the polar data directly. FIG. 8 is a spatial representation of image data planes a,b,c, . . . n seen edge-on, in the same manner as FIG. 6. The volumetric data is viewed from a display plane 58, also seen edge-on. In the spatial representation the viewing raylines 272–276 are seen to be parallel in the spatial domain, intersecting the image data planes as indicated by the darkened dots in the drawing.

Figure 9:
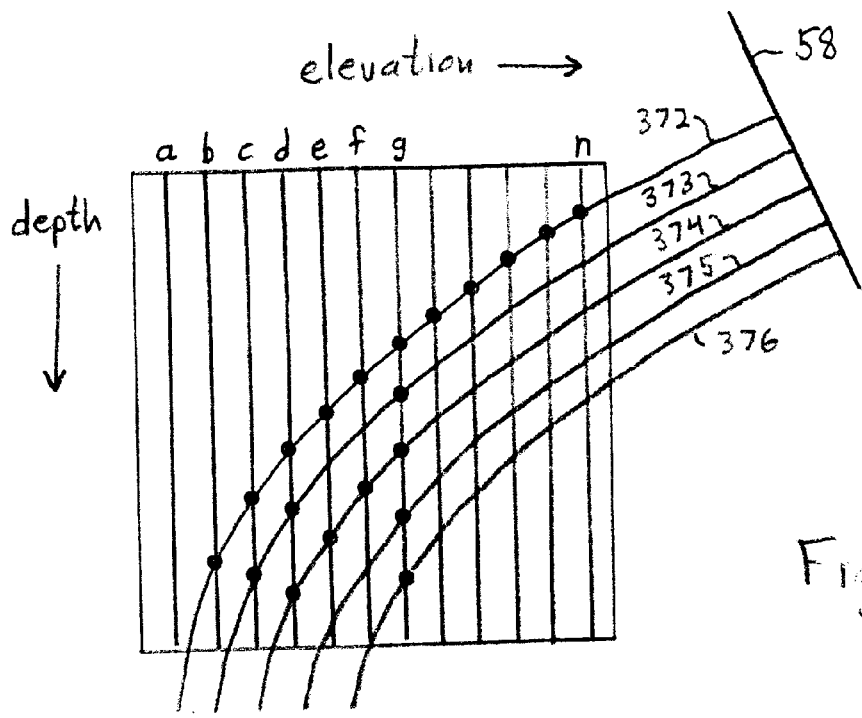
FIG. 9 illustrates the image data planes a,b,c, . . . n in the polar domain and drawn in parallel.

FIG. 9 illustrates the image data planes a,b,c, . . . n in the polar domain and drawn in parallel. In the polar domain the raylines 372–376 from the display plane 58 are seen to be parallel, but curved. The intersections of the raylines and the image data planes are again indicated by the darkened dots. These data values can be obtained directly from received ultrasound data by changing the sample clock along each ultrasound beam so that the correct sample values is put in memory for access by the rendering process. The delays of the sample clock can be pre-computed according to the selected view plane, then accessed when the view plane is chosen. The delay times between samples on each beam are seen to vary along each beam and are not uniform in the polar domain.

The warping of the projected raylines can be pre-computed for a given volumetric orientation or can be computed in real time as it is needed. The warping can be accomplished in an address look-up table for the rendering operation, for instance.

When a plurality of sector images are acquired in a rotating or fanned acquisition it will be appreciated that the data may be angularly variable in two dimensions: from scanline to scanline within a sector plane and from plane to plane within the rotated or fanned image planes. It is within the scope of the present invention to perform normal 2D scan conversion on each image plane, then to warp the rendering raylines to account only for the plane to plane angulation, or to perform no scan conversion at all and to account for both scanline-to-scanline and plane-to-plane angularity in the rayline warping. The choice to do some or no scan conversion is a design choice which can vary from one application to another depending upon the hardware available, the image display rate, and other variables.

What is claimed is:

1. An ultrasound system which produces diagnostic images of volumetric regions of the body comprising:
    a probe which acquires echo signals along scanlines which are angularly arrayed with respect to each other from a volumetric region;
    a data storage device responsive to the echo signals which stores 3D data acquired from the volumetric region; and
    a volume renderer responsive to the 3D data which renders a 3D image using projections through the 3D data which are warped to account for an angular acquisition geometry.

2. The ultrasound system of claim 1, wherein the projections comprise sequences of data values which are accumulate by a rendering function.

3. The ultrasound system of claim 2, wherein the rendering function comprises one of a compositing, integrating, averaging, or peak detecting function.

4. The ultrasound system of claim 2, wherein the data values of each sequence have addresses and wherein each sequence of data values is nonlinear in polar coordinates.

5. The ultrasound system of claim 1, wherein the projections of the volume renderer produce pixels of a 3D image, and further comprising a display responsive to the volume renderer which displays a 3D image of the volumetric region.

6. The ultrasound system of claim 5, wherein the 3D image comprises a 3D projection, orthographic, or perspective image.

7. The ultrasound system of claim 5, wherein the 3D image comprises a planar image of a plane through the volumetric region.

8. An ultrasound system which produces diagnostic images of volumetric regions of the body comprising:
    a probe which acquires echo signals along scanlines which are angularly arrayed with respect to each other from a volumetric region;
    a data storage device responsive to the echo signals which stores 3D data acquired from the volumetric region; and
    a volume renderer responsive to the 3D data which renders a 3D image using projections through the 3D data which are warped to account for an angular acquisition geometry,
    wherein the volume renderer comprises a volume renderer which operates on 3D data exhibiting non-Cartesian coordinates in at least one dimension,
    wherein the projections are warped to account for the non-Cartesian coordinates.

9. The ultrasound system of claim 8, wherein the non-Cartesian coordinates comprise polar coordinates.

10. An ultrasound system which produces diagnostic images of volumetric regions of the body comprising:
    a probe which acquires echo signals along scanlines which are angularly arrayed with respect to each other from a volumetric region;
    a data storage device responsive to the echo signals which stores 3D data acquired from the volumetric region; and
    a volume renderer responsive to the 3D data which renders a 3D image using projections through the 3D data which are warped to account for an angular acquisition geometry,
    further comprising a scan converter responsive to the angularly arrayed scanlines which converts polar data to Cartesian coordinates in a first dimension,
    wherein the volume renderer comprises a volume renderer which renders a 3D image from data converted by the scan converter using projections which are warped to account for an angular acquisition geometry in a second dimension.

11. The ultrasound system of claim 10, wherein the scan converter comprises a 2D scan converter which converts sector scanned image data in an image plane, wherein the projection warping accounts for image plane to image plane angular variation.

12. A method for producing three dimensional ultrasonic images comprising:

acquiring echo data from a volumetric region along a plurality of angularly arranged scanlines;

producing a 3D data set from the echo data; and rendering a 3D image from the 3D data set by means of projected raylines which are warped to account for the angular variation of the scanlines.

13. The method of claim 12, wherein rendering further comprises accumulating the values of data at addresses intersected by the projected raylines.

14. The method of claim 13, further comprising forming a 3D image from the accumulated data values.

15. A method for producing three dimensional ultrasonic images comprising:

acquiring echo data from a volumetric region along a plurality of angularly arranged scanlines;

producing a 3D data set from the echo data; and rendering a 3D image from the 3D data set by means of projected raylines which are warped to account for the angular variation of the scanlines, wherein the projected raylines exhibit polar coordinates, and wherein rendering comprises rendering a 3D image by means of raylines comprising data address sequences which are nonlinear in polar space.

16. The method of claim 15, wherein rendering comprises rendering a 3D image by means of projected raylines which are warped to emulate the path of a linear rayline through Cartesian space.

17. An ultrasound system which produces diagnostic images of volumetric regions of the body comprising:

a probe which is moved to acquire a sequence of angularly displaced sector images from a volumetric region;

a scan converter which converts the data of each sector image to Cartesian coordinates;

a data storage device responsive to the converted sector images which stores 3D data acquired from the volumetric region; and a volume renderer responsive to the 3D data which renders a 3D image using projections through the 3D data which are warped to account for the angular displacement of the sector images.

18. An ultrasound system which produces diagnostic images of volumetric regions of the body comprising:

a probe which is moved to acquire a sequence of angularly displaced linear array images from a volumetric region;

a scan converter which converts the data of each linear array image to Cartesian coordinate data;

a data storage device responsive to the converted linear array images which stores 3D data acquired from the volumetric region; and a volume renderer responsive to the 3D data which renders a 3D image using projections through the 3D data which are warped to account for the angular displacement of the linear array images.

19. An ultrasound system which produces diagnostic images of volumetric regions of the body comprising:

a multi dimensional array of transducer elements which electronically steers scanlines in different angular directions through a volumetric region being imaged;

a data storage device responsive to the scanline data images which stores 3D data acquired from the volumetric region; and a volume renderer responsive to the 3D data which renders a 3D image using projections through the 3D data which are warped to account for the angular displacement of the scanlines.

* * * * *